(12) United States Patent
Lim et al.

(10) Patent No.: US 12,059,941 B2
(45) Date of Patent: Aug. 13, 2024

(54) VENTILATION SEAT OF VEHICLE

(71) Applicant: HYUNDAI TRANSYS INCORPORATED, Seosan-si (KR)

(72) Inventors: Ho Sub Lim, Hwaseong-si (KR); Sun Woo Kim, Hwaseong-si (KR); Tae Hyoung Yang, Hwaseong-si (KR); In Ho Lee, Hwaseong-si (KR); Hwa Jun Lee, Hwaseong-si (KR)

(73) Assignee: HYUNDAI TRANSYS INCORPORATED, Seosan-si (KR)

( * ) Notice: Subject to any disclaimer, the term of this patent is extended or adjusted under 35 U.S.C. 154(b) by 226 days.

(21) Appl. No.: 17/684,653

(22) Filed: Mar. 2, 2022

(65) Prior Publication Data

US 2022/0281284 A1    Sep. 8, 2022

(30) Foreign Application Priority Data

Mar. 5, 2021    (KR) .................. 10-2021-0029398

(51) Int. Cl.
*B60H 1/00*    (2006.01)
*A61L 9/20*    (2006.01)

(52) U.S. Cl.
CPC .......... *B60H 1/00285* (2013.01); *A61L 9/205* (2013.01); *B60H 1/00028* (2013.01); *B60H 1/00564* (2013.01); *B60H 2001/00078* (2013.01)

(58) Field of Classification Search
CPC ................ B60H 1/00285; A61L 9/205; A61L 2209/16; B60N 2/56; B60N 2/5635
See application file for complete search history.

(56) References Cited

U.S. PATENT DOCUMENTS

| 2005/0282486 A1* | 12/2005 | Takeda | B60N 2/56 |
| | | | 454/158 |
| 2011/0319004 A1* | 12/2011 | Kim | A47C 7/744 |
| | | | 454/162 |
| 2014/0179212 A1* | 6/2014 | Space | B60N 2/5635 |
| | | | 454/76 |
| 2017/0036516 A1* | 2/2017 | Kim | B60H 3/0658 |
| 2022/0054699 A1* | 2/2022 | Nakama | F24F 7/003 |

FOREIGN PATENT DOCUMENTS

| CN | 105473360 A | 4/2016 |
| CN | 205130871 U | 4/2016 |
| CN | 108656891 A | 10/2018 |

(Continued)

*Primary Examiner* — David R Dunn
*Assistant Examiner* — Tania Abraham
(74) *Attorney, Agent, or Firm* — Bridgeway IP Law Group, PLLC; Jihun Kim

(57) ABSTRACT

A ventilation seat of a vehicle is proposed. The ventilation seat includes a ventilation duct assembly mounted to a seat of the vehicle and configured to suck indoor air and to discharge air toward a vehicle room or a surface of the seat, an air cleaning assembly arranged in an air flow path of the ventilation duct assembly and configured to clean air passing through the air flow path in operation thereof, and a controller configured to operate the ventilation duct assembly in operation of an air cleaning mode of the vehicle to generate an air flow flowing through the seat, and configured to operate the air cleaning assembly to allow the air flow of the ventilation duct assembly to clean air in the vehicle.

10 Claims, 2 Drawing Sheets

(56) References Cited

FOREIGN PATENT DOCUMENTS

| | | | | |
|---|---|---|---|---|
| CN | 212233805 U | 12/2020 | | |
| JP | 6669845 B1 | * 3/2020 | ............. | A61L 9/205 |
| KR | 10-2008-0048911 A | 6/2008 | | |
| KR | 10-2010-0010265 A | 2/2010 | | |
| KR | 10-2012-0002300 A | 1/2012 | | |
| KR | 10-2012-0086809 A | 8/2012 | | |
| KR | 10-1851522 B1 | 4/2018 | | |

* cited by examiner

VENTILATION SEAT OF VEHICLE

CROSS REFERENCE TO RELATED APPLICATION

The present application claims priority to Korean Patent Application No. 10-2021-0029398, filed Mar. 5, 2021, the entire contents of which is incorporated herein for all purposes by this reference.

BACKGROUND OF THE INVENTION

Field of the Invention

The present invention relates generally to a ventilation seat of a vehicle, which is provided in a seat of the vehicle and configured to clean air passing through an air cleaning assembly by using a photocatalyst in operation of ventilation duct assembly and to discharge cleaned air toward a seating surface of the seat or the vehicle room.

Description of the Related Art

Conventionally, general air conditioners and heaters are used as air conditioning in a vehicle. Furthermore, a ventilation seat for convenience of each occupant is widely used. The ventilation seat discharges gas from a seating surface of the seat, thereby cooling the seat in direct contact with the occupant.

On the other hand, when air inside the vehicle is polluted with microorganisms, nitrogen oxides, exhaust gas, fine dust, odors, etc. due to occupant's use of the vehicle or the indoor and outdoor environment of the vehicle, the above pollution adversely affects the occupant, and importance of technology related to air cleaning in a vehicle is increasing recently.

In order to solve the above problem, a filter for air cleaning can be provided inside the ventilation seat, but a type of filter used in the ventilation seat, amount of filter, a location of filter, etc. may be limited due to characteristics of the ventilation seat that should be driven with low power and low noise. Therefore, it is necessary to develop a seat air conditioning system that minimizes the above problems and has high air cleaning efficiency.

The foregoing described as the controller and the controlling method of operating a fuel cell is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problem occurring in the related art, and the present invention is intended to provide a ventilation seat of a vehicle, wherein a ventilation duct assembly, an air cleaning assembly, and a controller are provided in a seat of the vehicle, and when the ventilation duct assembly is operated, heated air or cooled air is discharged toward a seating surface of the seat through a heat conductor, and air passing through the air cleaning assembly is cleaned using a photocatalyst, and cleaned air is discharged toward the seating surface of the seat or the vehicle room to achieve both seat air conditioning and air cleaning.

In order to achieve the above objective, according to one aspect of the present invention, there is provided a ventilation seat of a vehicle, the ventilation seat including: a ventilation duct assembly mounted to a seat of the vehicle and configured to suck indoor air and to discharge air toward a vehicle room or a surface of the seat; an air cleaning assembly arranged in an air flow path of the ventilation duct assembly and configured to clean air passing through the air flow path in operation thereof; and a controller configured to operate the ventilation duct assembly in operation of an air cleaning mode of the vehicle to generate an air flow flowing through the seat, and configured to operate the air cleaning assembly to allow the air flow of the ventilation duct assembly to clean air in the vehicle.

The ventilation duct assembly may include a blower at an end thereof, and the controller may control the blower so that the ventilation duct assembly may be operated to suck indoor air and discharge air to the vehicle room or the surface of the seat.

The air cleaning assembly may include a catalytic converter configured to clean air passing through the air flow path when light is emitted in the air flow path, and a light source assembly arrange on an inner wall of the air flow path to face the catalytic converter and configured to emit the light to the catalytic converter.

A material containing a photocatalyst may be put on the catalytic converter, and as the light emitted from the light source assembly reaches to the photocatalyst, air may be cleaned.

The light source assembly may include at least one light source, and the at least one light source may be configured to emit light to an entire surface of the catalytic converter that faces the light source assembly.

An expansion portion may be provided in the air flow path of the air cleaning assembly in a direction in which air flows, the expansion portion being shaped such that the air flow path expands and contracts, and the catalytic converter may be provided at the expansion portion.

The light source assembly may include a plurality of light sources on an inner wall of the expansion portion, and the catalytic converter may be arranged in a width direction of the air flow path of the air cleaning assembly.

The ventilation duct assembly may include an inlet through which air is introduced from the vehicle room, a first outlet through which air is discharge into the vehicle room, and a second outlet through which air is discharged toward the surface of the seat, wherein the air cleaning assembly may be arranged in the inlet or the first outlet.

A heat conductor may be provided in the air flow path of the ventilation duct assembly and divide the air flow path and be configured to heat or cool air passing through each of divided air flow paths, and each of the divided air flow paths may be connected to the vehicle room or the surface of the seat.

The controller may detect whether an occupant is seated on the seat by using a seating sensor provided in the seat, and when seating of the occupant on the seat is detected, the controller may receive the air cleaning mode from the occupant, and the controller may operate the ventilation duct assembly or the air cleaning assembly in response to the input air cleaning mode.

When seating of the occupant on the seat is not detected, the controller may operate the ventilation duct assembly and the air cleaning assembly to clean indoor air of the vehicle.

According to the ventilation seat of a vehicle of the present invention, the ventilation duct assembly, the air cleaning assembly, and the controller are provided in the seat of the vehicle, and when the ventilation duct assembly is operated, heated air or cooled air is discharged toward the seating surface of the seat by the heat conductor, and air passing through the air cleaning assembly is cleaned using a photocatalyst, and cleaned air is discharged toward the seating surface of the seat or the vehicle room, thereby performing both the seat air conditioning and air cleaning.

BRIEF DESCRIPTION OF THE DRAWINGS

The above and other objectives, features, and other advantages of the present invention will be more clearly understood from the following detailed description when taken in conjunction with the accompanying drawings, in which.

DETAILED DESCRIPTION OF THE INVENTION

Figure 1:
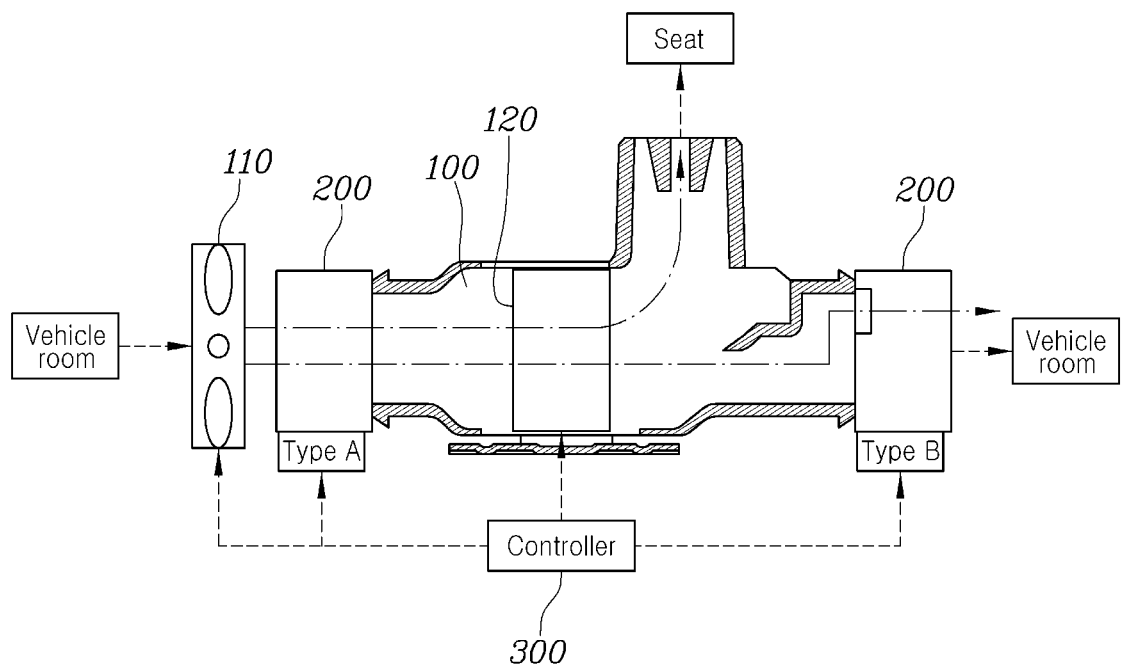
FIG. 1 is a view showing a ventilation seat of a vehicle according to an embodiment of the present invention.
Figure 2:
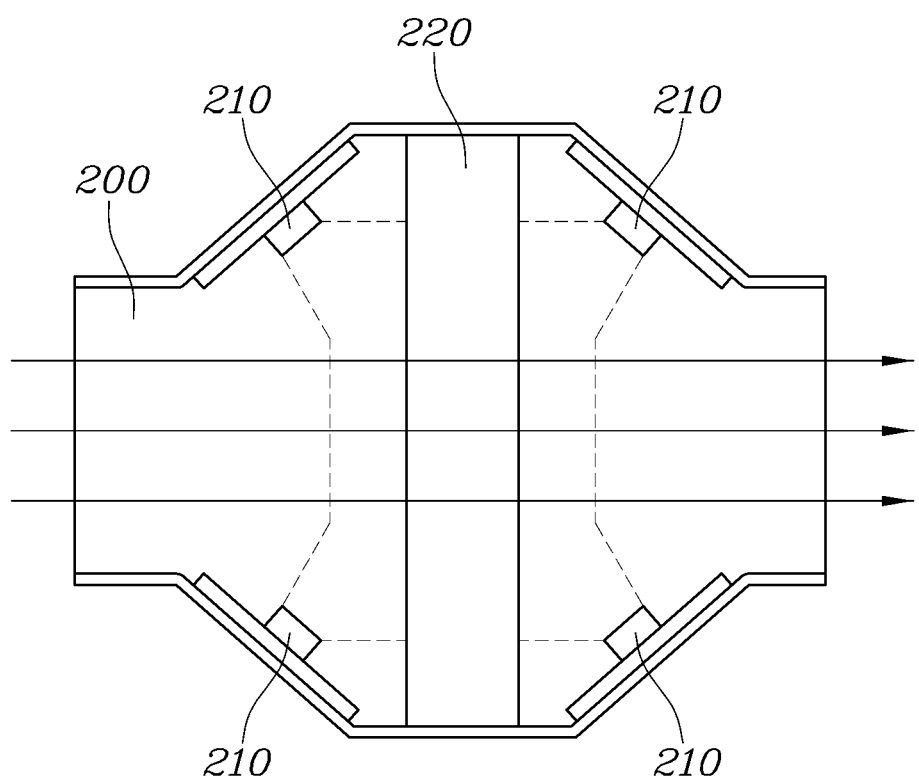
FIG. 2 is a view showing an air cleaning assembly of the ventilation seat of a vehicle according to the embodiment of the present invention.

FIG. 1 is a view showing a ventilation seat of a vehicle according to an embodiment of the present invention. FIG. 2 is a view showing an air cleaning assembly of the ventilation seat of a vehicle according to the embodiment of the present invention.

FIG. 1 is a view showing a ventilation seat of a vehicle according to an embodiment of the present invention.

According to the embodiment of the present invention, the ventilation seat of a vehicle includes: a ventilation duct assembly 100 mounted to a seat of the vehicle and configured to suck indoor air and to discharge air toward a vehicle room or a surface of the seat; an air cleaning assembly 200 arranged in an air flow path of the ventilation duct assembly 100, and configured to clean air passing through the air flow path; and a controller 300 configured to operate the ventilation duct assembly 100 in operation of an air cleaning mode of the vehicle to generate an air flow flowing through the seat, and configured to operate the air cleaning assembly 200 to allow the air flow of the ventilation duct assembly 100 to clean the indoor air in the vehicle.

Furthermore, according to the embodiment of the present invention, a blower 110 is provided at an end of the ventilation duct assembly 100 of the ventilation seat of a vehicle. The controller 300 controls the blower 110 so that the ventilation duct assembly 100 may be operated to suck the indoor air of the vehicle and to discharge air toward the vehicle room or the surface of the seat.

Specifically, the controller 300 operates the blower 110 so that the indoor air of the vehicle is introduced into the air flow path of the ventilation duct assembly 100. The inside of the ventilation duct assembly 100 is divided and the branched portions are respectively connected to the seat and the vehicle room, so that the introduced air is discharged toward the seating surface of the seat or the vehicle room. In the above-described process, when the controller 300 operates the air cleaning assembly 200 according to the air cleaning mode, polluted air in the vehicle room is cleaned (sterilization, deodorization, etc.) while passing through the air cleaning assembly 200, and cleaned air is discharged toward the seating surface of the seat or the vehicle room again. Therefore, according to the embodiment of the present invention, the ventilation seat of a vehicle performs both an existing function as the ventilation seat and a function as vehicle air cleaning.

FIG. 2 is a view showing an air cleaning assembly of the ventilation seat of a vehicle according to the embodiment of the present invention. According to the embodiment of the present invention, the air cleaning assembly 200 of the ventilation seat of a vehicle may include a catalytic converter 220 and a light source assembly 210. When light is emitted from the inside of the air flow path, the catalytic converter 220 cleans air passing through the air flow path, and the light source assembly 210 is arranged on an inner wall of the air flow path to face the catalytic converter 220 and configured to emit light to the catalytic converter 220.

Furthermore, a material containing a photocatalyst is put on the catalytic converter 220, and as the light emitted from the light source assembly 210 reaches to the photocatalyst, the air is cleaned. At least one light source 210 is provided, the at least one light source 210 may emit the light toward an entire surface of the catalytic converter 220 facing the at least one light source 210.

Specifically, the photocatalyst is a compound that absorbs light energy to initiate a photochemical reaction and promotes a photochemical reaction as a catalyst. When light is emitted, the photocatalyst has effects such as sterilization or deodorization. Herein, the light source assembly 210 may consist of an LED module, and the LED module is a device that splits light waves with a wavelength of 380 nm or less and emits light at a UV-A level. The photocatalyst may be titanium oxide (TiO2). A plurality of light sources 210 is provided to face the catalytic converter 220 in the inside of the air cleaning assembly 200 while having predetermined spectral angles (e.g., 120 degrees). Therefore, the plurality of light sources 210 may emit light to the entire surface of the catalytic converter 220 to increase air cleaning efficiency.

Meanwhile, according to the embodiment of the present invention, the air cleaning assembly 200 of the ventilation seat of a vehicle has an expansion portion (no reference numeral) in the air flow path thereof. The expansion portion is formed such that the air flow path expands and contracts in a direction in which air flows. The catalytic converter 220 may be provided in the expansion portion. The plurality of light sources 210 is provided on an inner wall of the expansion portion, and the catalytic converter 220 may be arranged in a width direction of the air flow path of the air cleaning assembly 200.

Referring to FIG. 2, as the catalytic converter 220 is arranged in the width direction crossing the air flow path, a contact area in contact with the catalytic converter 220 is significantly increased. Herein, the catalytic converter 220 is formed in a porous structure. When the light is emitted from the light source assembly 210, air passing through the inside of the catalytic converter 220 may be cleaned.

Furthermore, when the air flow path expands, a flow rate of the air passing through the air cleaning assembly 200 is reduced at the expansion portion, and thus the air cleaning efficiency of the air passing through the catalytic converter 220 may be increased. Meanwhile, the catalytic converter 220 is formed in a structure such as the porous structure minimizing air resistance, thereby minimizing the effect on ventilation performance of the catalytic converter 220 in operation of the ventilation seat.

Meanwhile, according to the embodiment of the present invention, the ventilation duct assembly 100 of the ventilation seat of a vehicle includes an inlet through which air is introduced from the vehicle room, a first outlet through which air is discharged into the vehicle room, and a second outlet through which air is discharged toward the surface of the seat. The air cleaning assembly 200 may be arranged in the inlet or the first outlet. When the air cleaning assembly 200 is located in the inlet (FIG. 1, Type A), both air discharged into the seat and the vehicle room are cleaned, which is an advantage, but the ventilation performance of the ventilation seat to discharge air through the vehicle seat may be slightly affected.

Meanwhile, the air cleaning assembly 200 is arranged in the first outlet (FIG. 1, Type B), the ventilation performance of the ventilation seat to discharge air to the vehicle seat is not affected, but air discharged to the seating surface of the seat is not cleaned, which is an disadvantage. Type A, B may be selected in response to a ventilation seat structure, ventilation performance, air resistance of the air cleaning assembly 200, and air cleaning efficiency, etc.

Furthermore, according to the embodiment of the present invention, the ventilation seat of a vehicle includes a heat conductor 120 in the air flow path of the ventilation duct assembly 100. The heat conductor 120 divides the air flow path and heats or cools air passing through each of divided air flow paths. The divided air flow paths may be respectively connected to the vehicle room and the surface of the seat. The heat conductor 120 is made of a thermoelectric element and the controller 300 controls the heat conductor 120 to heat or cool air discharged toward the seating surface of the seat.

As the air flow path is divided, heated and cooled air flows in each flow path. Specifically, when air discharged toward the seat is heated, air discharged toward the vehicle room is cooled, and when air discharged toward the seat is cooled, air discharged toward the vehicle is heated. The controller 300 controls the heat conductor 120 and the ventilation duct assembly 100 to discharge air heated or cooled toward the seat and in response to a request of an occupant seated on the seat. In addition, the controller 300 operates the air cleaning assembly 200 to discharge cleaned air.

Meanwhile, according to the embodiment of the present invention, the controller 300 of the ventilation seat of a vehicle detects whether the occupant is seated on the seat by a seating sensor provided in the seat. When seating of the occupant on the seat is detected, the controller receives the air cleaning mode, and the controller may operate the ventilation duct assembly 100 or the air cleaning assembly 200 in response to the air cleaning mode. When the controller 300 detects no seating of the occupant on the seat, the controller 300 may operate the ventilation duct assembly 100 and the air cleaning assembly 200 to clean indoor air of the vehicle.

In detail, the controller 300 may control both vehicle room air conditioning and seat air conditioning. When the occupant inputs the air cleaning mode, the controller controls the air cleaning function by the vehicle room air conditioning, the seat air conditioning in response to the air cleaning mode. For example, the controller 300 may perform: the air cleaning mode of operating the indoor air conditioning when an occupant is seated on the seat and needs both the indoor air conditioning and the seat air conditioning; an integrated air conditioning mode of operating all the ventilation duct assembly 100, the blower 110, the heat conductor 120, and the air cleaning assembly; the indoor air cleaning mode of operating the indoor air conditioning and only the ventilation duct assembly 100, the blower 110, and the air cleaning assembly; and the seat air conditioning mode of operating only the ventilation duct assembly 100, the blower 110, the heat conductor 120, and the air cleaning assembly. The controller may perform a general seat air conditioning mode without the air cleaning assembly.

Furthermore, when an occupant is not seated on the seat, the seat air conditioning is unnecessary, so that the controller 300 may operate only the ventilation duct assembly 100, the blower 110, and the air cleaning assembly 200, thereby efficiently and rapidly cleaning indoor air by the seat without an occupant. In addition, the controller 300 measures an air pollution level by an air pollution sensor, and when the controller 300 detects air pollution above a predetermined level, the controller 300 immediately operates the air cleaning mode of both a seat with an occupant and a seat without an occupant, thereby performing a smarter vehicle room air conditioning function.

Although the preferred embodiment of the present invention has been disclosed for illustrative purposes, those skilled in the art will appreciate that various modifications, additions, and substitutions are possible, without departing from the spirit and scope of the present invention.

What is claimed is:

1. A ventilation seat of a vehicle, the ventilation seat comprising:
   a ventilation duct assembly mounted to a seat of the vehicle and configured to suck air and to discharge the air toward a vehicle room or a surface of the seat;
   an air cleaning assembly disposed in an air flow path of the ventilation duct assembly and configured to clean the air passing through the air flow path in operation thereof; and
   a controller configured to operate the ventilation duct assembly in operation of an air cleaning mode of the vehicle to generate an air flow flowing through the seat, and configured to operate the air cleaning assembly to allow the air flow of the ventilation duct assembly to clean air in the vehicle,
   wherein the air cleaning assembly includes a catalytic converter configured to clean the air passing through the air flow path when light is emitted in the air flow path, and a light source assembly disposed on an inner wall of the air flow path to face the catalytic converter and configured to emit light to the catalytic converter, and
   wherein the air cleaning assembly includes an expansion portion disposed in the air flow path of the air cleaning assembly in a direction in which the air flows, the expansion portion being shaped to enable that the air flow path expands and contracts, and wherein the catalytic converter is disposed at the expansion portion.

2. The ventilation seat of claim 1, wherein the ventilation duct assembly comprises a blower disposed at an end thereof, and the controller is configured to control the blower to operate the ventilation duct assembly to suck the air and discharge the air to the vehicle room or the surface of the seat.

3. The ventilation seat of claim 1, wherein the catalytic converter has a material containing a photocatalyst, and the air cleaning assembly is configured to clean the air as the light emitted from the light source assembly reaches to the photocatalyst.

4. The ventilation seat of claim 1, wherein the light source assembly comprises at least one light source, and the at least one light source is configured to emit light to an entire surface of the catalytic converter that faces the light source assembly.

5. The ventilation seat of claim 1, wherein the light source assembly comprises a plurality of light sources disposed on an inner wall of the expansion portion, and the catalytic converter is disposed in a width direction of the air flow path of the air cleaning assembly.

6. The ventilation seat of claim 1, wherein the ventilation duct assembly comprises an inlet configured to introduce the air therethrough from the vehicle room, a first outlet configured to discharge the air therethrough into the vehicle room, and a second outlet configured to discharge the air therethrough toward the surface of the seat, wherein the air cleaning assembly is disposed in the inlet or the first outlet.

7. The ventilation seat of claim 1, wherein a heat conductor is disposed in the air flow path of the ventilation duct assembly, the heat conductor being configured to divide the air flow path and to heat or cool air passing through each of divided air flow paths, wherein each of the divided air flow paths is connected to the vehicle room or the surface of the seat.

8. The ventilation seat of claim 1, wherein the controller is configured to detect whether an occupant is seated on the seat by using a seating sensor disposed in the seat, and when seating of the occupant on the seat is detected, the controller is configured to receive the air cleaning mode from the occupant, and the controller is configured to operate the ventilation duct assembly or the air cleaning assembly in response to the air cleaning mode.

9. The ventilation seat of claim 8, wherein when seating of the occupant on the seat is not detected, the controller is configured to operate the ventilation duct assembly and the air cleaning assembly to clean indoor air of the vehicle.

10. A ventilation seat of a vehicle, the ventilation seat comprising:
- a ventilation duct assembly mounted to a seat of the vehicle and configured to suck air and to discharge the air toward a vehicle room or a surface of the seat;
- an air cleaning assembly disposed in an air flow path of the ventilation duct assembly and configured to clean the air passing through the air flow path in operation thereof; and
- a controller configured to operate the ventilation duct assembly in operation of an air cleaning mode of the vehicle to generate an air flow flowing through the seat, and configured to operate the air cleaning assembly to allow the air flow of the ventilation duct assembly to clean air in the vehicle,
- wherein the controller is configured to detect whether an occupant is seated on the seat by using a seating sensor disposed in the seat, and when seating of the occupant on the seat is detected, the controller is configured to receive the air cleaning mode from the occupant, and the controller is configured to operate the ventilation duct assembly or the air cleaning assembly in response to the air cleaning mode, and
- wherein when seating of the occupant on the seat is not detected, the controller is configured to operate the ventilation duct assembly and the air cleaning assembly to clean indoor air of the vehicle.

* * * * *